United States Patent
Fu et al.

(10) Patent No.: US 7,539,583 B2
(45) Date of Patent: May 26, 2009

(54) METHOD AND SYSTEM FOR DEFECT DETECTION

(75) Inventors: Yonghang Fu, Plano, TX (US); Yongqiang Liu, Plano, TX (US); Michael J. Darwin, Beaverton, OR (US)

(73) Assignee: Rudolph Technologies, Inc., Flanders, NJ (US)

( * ) Notice: Subject to any disclaimer, the term of this patent is extended or adjusted under 35 U.S.C. 154(b) by 281 days.

(21) Appl. No.: 11/201,279

(22) Filed: Aug. 10, 2005

(65) Prior Publication Data

US 2006/0199287 A1  Sep. 7, 2006

Related U.S. Application Data

(60) Provisional application No. 60/658,914, filed on Mar. 4, 2005.

(51) Int. Cl.
*G01N 37/00* (2006.01)

(52) U.S. Cl. .................. 702/81; 702/182; 438/16; 382/144; 382/145

(58) Field of Classification Search ............. 702/35, 702/36, 40, 81–84, 117, 118, 172, 179; 382/144, 382/145, 147–151; 356/237.4, 237.5; 700/108–111; 438/16

See application file for complete search history.

(56) References Cited

U.S. PATENT DOCUMENTS

| 5,539,752 A | * | 7/1996 | Berezin et al. ............. 714/724 |
| 5,619,429 A | * | 4/1997 | Aloni et al. ................. 700/279 |
| 5,982,920 A | * | 11/1999 | Tobin et al. ................. 382/145 |
| 6,246,788 B1 | * | 6/2001 | Pattikonda et al. .......... 382/147 |
| 6,292,260 B1 | | 9/2001 | Lin et al. |
| 6,292,582 B1 | | 9/2001 | Lin et al. |
| 6,483,938 B1 | | 11/2002 | Hennessey et al. |
| 6,487,307 B1 | | 11/2002 | Hennessey et al. |
| 6,818,376 B2 | | 11/2004 | Lee et al. |

* cited by examiner

*Primary Examiner*—Manuel L Barbee
(74) *Attorney, Agent, or Firm*—Dicke, Billig & Czaja, PLLC

(57) ABSTRACT

A method for inspecting objects such as semiconductor wafers. A staging platform and an optical platform are arranged so that the object may be staged and its surface scanned by optical equipment situated on the optical platform. During the scanning process, the surface is illuminated with light of a plurality of wavelengths, each strobed at a predetermined rate so that multiple images may be collected using time and frequency multiplexing. The multiple images are stored in a database for analysis, which includes processing selected ones of the multiple images according to one or more algorithms. The defect-detection algorithms used for each object are determined by referenced to a predetermined or calculated defect detection protocol, then a defect mask is created for each pixel in the images that is suspected to be defective. The defect mask is then compared to threshold parameters to determine which if any of the suspected defects should be reported.

19 Claims, 5 Drawing Sheets

METHOD AND SYSTEM FOR DEFECT DETECTION

This application claims the benefit of U.S. Provisional Application No. 60/658,914 filed on 4 Mar. 2005, the disclosure of which is hereby incorporated by reference.

TECHNICAL FIELD

The present invention is directed generally to the field of defect detection, and more specifically to a method and system for inspecting objects such as semiconductor wafers or printed circuit boards to detect defects using an automated inspection system that yields a high degree of statistical confidence in the result, thus ensuring that as many defects as possible are discovered, and also that non-defective products are not erroneously identified for discard or repair.

BACKGROUND

There are many kinds of electrical and electronic devices that are widely available for scientific, business, and consumer-oriented applications. Rapid advances in technology have allowed their use to migrate from universities and large institutions to small businesses and homes. Computers are now popular, even for use by children, and a myriad of different telephones, televisions, games and gadgets may now be found in almost every household in the country. The new technology has not only made such applications possible, but has also lowered the cost of electronic devices to the point where they can be produced in great numbers and are easily affordable.

A great many components used in building electronic products are currently mass-produced despite the fact that their successful manufacture depends on fabrication to extremely precise tolerances. Semiconductor wafers, for example, and the printed circuit boards on which they are mounted, require the formation of a huge number of very small surface structures. These structures are often formed automatically using mechanical or chemical means, that is, without direct human intervention. In the case of, for example, semiconductor wafers, these structures are formed by alternately removing select portions of a silicon substrate and applying additional materials or treating with chemical substances to produce surface structures having desirable properties. These structures are often so small that they can barely be seen, if at all, with the naked eye.

In one manufacturing operation, a material called photoresist (or simply "resist") is applied to the surface of a wafer that is being used to make semiconductor chips. FIG. 1 is an illustration of an exemplary wafer 100, shown in plan view. The wafer 100 is divided into a number of dice, for example die 105. The wafer 100 forms a flat edge (or simply "flat") 110 that may be used as a reference for locating specific points or dice, such as center point 115 or die 105. Resist may be deposited at center point 115 and the wafer 100 spun to evenly distribute the resist over its surface 101.

When the resist has been spread over the surface, it is selectively exposed to light emitted through a mask to create a pattern. The light causes changes in the resist so that when the surface is later rinsed, some of the resist will be washed away and some will remain. This forms a series of structures on surface 101 of wafer 100 (see FIG. 2). The wafer can then be treated, for example with a solution that etches away portions of the surface not covered with resist. Or additional materials may be deposited in similar fashion. This process is repeated until the desired components have been created on the surface of the wafer. It should be apparent that the structures made of resist or of other materials must be correctly formed onto the surface for the production process to create properly-functioning components. FIG. 2 is a side view of a small portion of wafer 100, illustrating the presence of a number of structures formed on surface 101. Although FIG. 2 is a cutaway view, it is only for illustration and not intended to represent any specific section of wafer 100. In addition, the actual size and location of structures 120, 121, and 122 are dependent on the specific application and their purpose in the production process. these structures may be formed of developed resist, or of materials deposited in the surface 101, or formed as a result of an etching process.

Because these surface structures are sometimes created in a series of reversible steps, identifying defects early may mean that corrective measures can be taken. And ultimately, finished products require inspection so that defective ones are not used. In the case of products such as semiconductor wafers, which frequently are used to for a number of separate components, portions identified as defective can be discarded while non-defective portions can be saved for eventual packaging and use. When production is finished (to an appropriate stage), the dice are separated and each individual die (along with a number of leads for providing electrical connections) is encapsulated in plastic to form a chip (not shown). Once manufactured, the chip will be programmed to perform one or more of the many functions for which they are used in electronic devices.

As should be apparent, a wafer therefore must undergo a fairly-large number of manufacturing steps before it is completed. During manufacturing, it also undergoes a corresponding number of test and inspections of various types. Although humans can and do inspect such products during the manufacturing process, often with the aid of a microscope or similar device, automated inspection systems are frequently desirable because they can perform the inspection much faster and, in some cases, more reliably. Optical inspection systems may be used in this role. Optical inspection systems, in general, capture images of the object being inspected after the object's surface has been illuminated by some form of light energy. The images may be examined by operators, and for this purpose may undergo some form of enhancement. Captured images, however, are often converted into digitized form for computer analysis.

This analysis may be done in a variety of ways. The images in digitized form may also be stored for future reference or converted back into a human-readable visual image. In general, computer analysis of captured images relies on the relative characteristics associated with each of a number of picture elements, or pixels. These pixels may be separately evaluated because they each represent the light received and converted into an electrical charge by one of many small photo-sensitive devices that are housed within a camera. To create a visual image, the data collected in this way by each of these individual pixels is aggregated to create a picture. Computer analysis is more flexible, because it can evaluate the pixel data more precisely and in a variety of ways. The captured image of a semiconductor wafer being evaluated may, for example, be compared to a previously-captured image of a 'perfect' wafer (which may have been generated by a computer rather than captured with a camera). Instead of the so-called golden-image comparison, some systems employ a die-to-die or frame-to-frame comparison. In these types of analyses, defective areas are identified simply because they deviate from other areas of the wafer that should yield a nearly-identical image.

Although other inspection methods may be employed, optical inspection has become very popular in electronics manufacturing operations and is widely used. Existing systems are far from perfect, however. For example, all optical imaging systems are limited in resolution by fundamental optical principles related to the wavelength of light, numerical aperture of the apparatus used, and by the overall geometry of the system. As components decrease in size, inspection tools are continually pushed to identify defects at or below their optimum optical resolution. In addition, even in an inspection process that simply compares a newly-captured image against a theoretically perfect reference, random variations can lead to noise sources in both the reference and newly acquired image thus leading to an overall reduction in defect detection sensitivity.

In addition, the analytical approach used is typically applied individually as the specific configuration and setup of hardware, software, and design strategy permits. Each of the defect detection schemes in current usage has its own strengths and weaknesses, and, depending on the defect signature, applicability. As a consequence, these approaches must often utilize complex filtering schemes in an attempt to reduce erroneous defects, sometimes at the expense of overall system resolution.

Needed then, is a methodology for more efficiently performing automated defect detection that provides greater statistical confidence in the result but does not greatly reduce system resolution. The present invention provides just such a solution.

SUMMARY OF THE INVENTION

To overcome the deficiencies in the prior art described above, the present invention provides an improved design for an optical inspection system. The present invention provides an improved design for maximizing sensitivity in defect detection while statistically increasing robustness. In one aspect, the present invention is a method for inspecting an object, and specifically a structure-bearing surface of an object, by scanning the object with an optical platform having one or more light sources for illuminating the object's surface and a camera for capturing one or more images of the illuminated object. The method also includes determining which of a number of available defect detection schemes to the data, or to subsets of the data, to determine within the capability of each scheme the presence of defects. Each scheme is assigned a weight value, and the method also includes defining one or more defect masks and building each mask by including in its value the weight associated with any defect detection scheme that identifies a defect. Preferably, there is a defect mask associated with each pixel of an image corresponding to an area on the surface of the wafer. After applying the defect detection schemes, the defect mask or masks are compared to a predetermined threshold and a confidence level in the existence of a defect in the area associated with the defect mask is thereby determined.

In another aspect, the present invention is a system for performing optical inspection. The system includes an optical platform having an image collection tool. The image collection tool is automated such that it can handle patterned semiconductor wafers. The image collection tool includes a sensor capable of line or area scanning of sample wafers across a predetermined electromagnetic wavelength range (in particular in the visible light spectrum). The sensor can be set up in parallel to perform multiple independent measurements of the same sample. The analysis tool is composed of one or more computers with data acquisition capability set up in parallel. The image collection and analysis tool (of specified resolution) is setup in a semiconductor process line after a key process step such as lithography. Images are collected and analyzed for each channel and one or more defect masks are created based on the results of the analysis. The defect mask or masks may then be compared to a predetermined threshold so that defects may be identified with greater accuracy.

In yet another aspect, the present invention is a system for inspecting the surface of an object including an optical platform for scanning the surface and a computing facility for analyzing data collected when the surface is scanned. The computing facility comprises a plurality of defect detection scheme modules for analyzing the collected data and a defect detection scheme manager for selecting which of the plurality of defect detection scheme modules to apply to the collected data. During the analysis the selected defect detection scheme modules are applied and at least one defect mask corresponding to a specific portion of the object surface being inspected is assigned a value determined by weights assigned to each of the defect detection modules applied to the collected data. The value of the defect mask is then compared to a threshold value to identify any surface defects.

A more complete appreciation of the present invention and the scope thereof can be obtained from the accompanying drawings and detailed description of the presently-preferred embodiments of the present invention.

BRIEF DESCRIPTION OF THE DRAWINGS

For a more complete understanding of the present invention, and the advantages thereof, reference is made to the following drawings in the detailed description below.

DETAILED DESCRIPTION OF ILLUSTRATIVE EMBODIMENTS

The present invention is directed to a method and system for performing inspections using an optical platform for collecting images of an object and then processing the images in a manner that produces a higher degree of confidence that the defects involving features formed on its surface, if any, have been properly identified. The present invention exploits multiple independent detection schemes and correlates them using a defect mask to increase detection sensitivity while decreasing unwanted nuisance defects. The method and system of the present invention are especially advantageous when applied to the inspection of semiconductor wafers and printed circuit boards during the production process.

The present invention will now be described in such an embodiment, that is, one useful for inspecting semiconductor wafers during the manufacturing process. The method and system of the present invention may, for example, be used to inspect wafers to which photoresist has been applied and developed to ensure that the photoresist has been properly developed. The present invention may, of course, also be applied elsewhere in the manufacturing process. By the same token, the principles involved may be useful in other types of inspection as well, such as in the manufacture of printed circuit boards.

Figure 1:
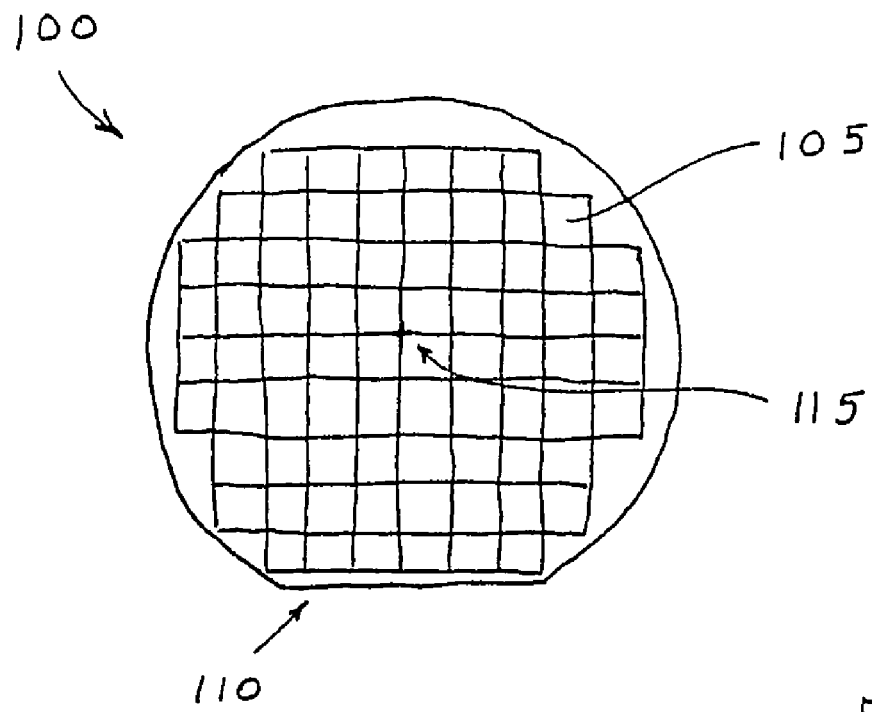
FIG. 1 is an illustration of an exemplary wafer, shown in plan view.
Figure 2:
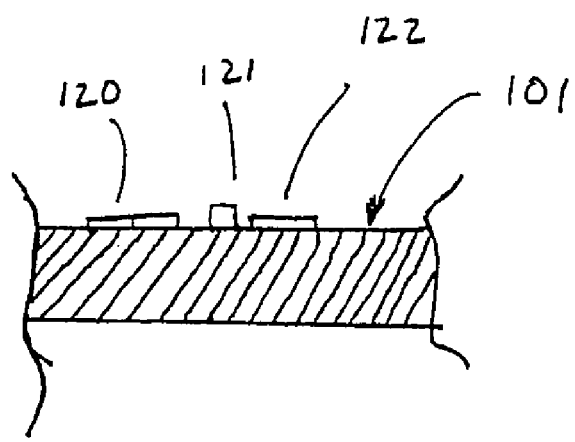
FIG. 2 is a side view of a small portion of the wafer of FIG. 1, illustrating the presence of a number of structures formed on the wafer's surface.
Figure 3:
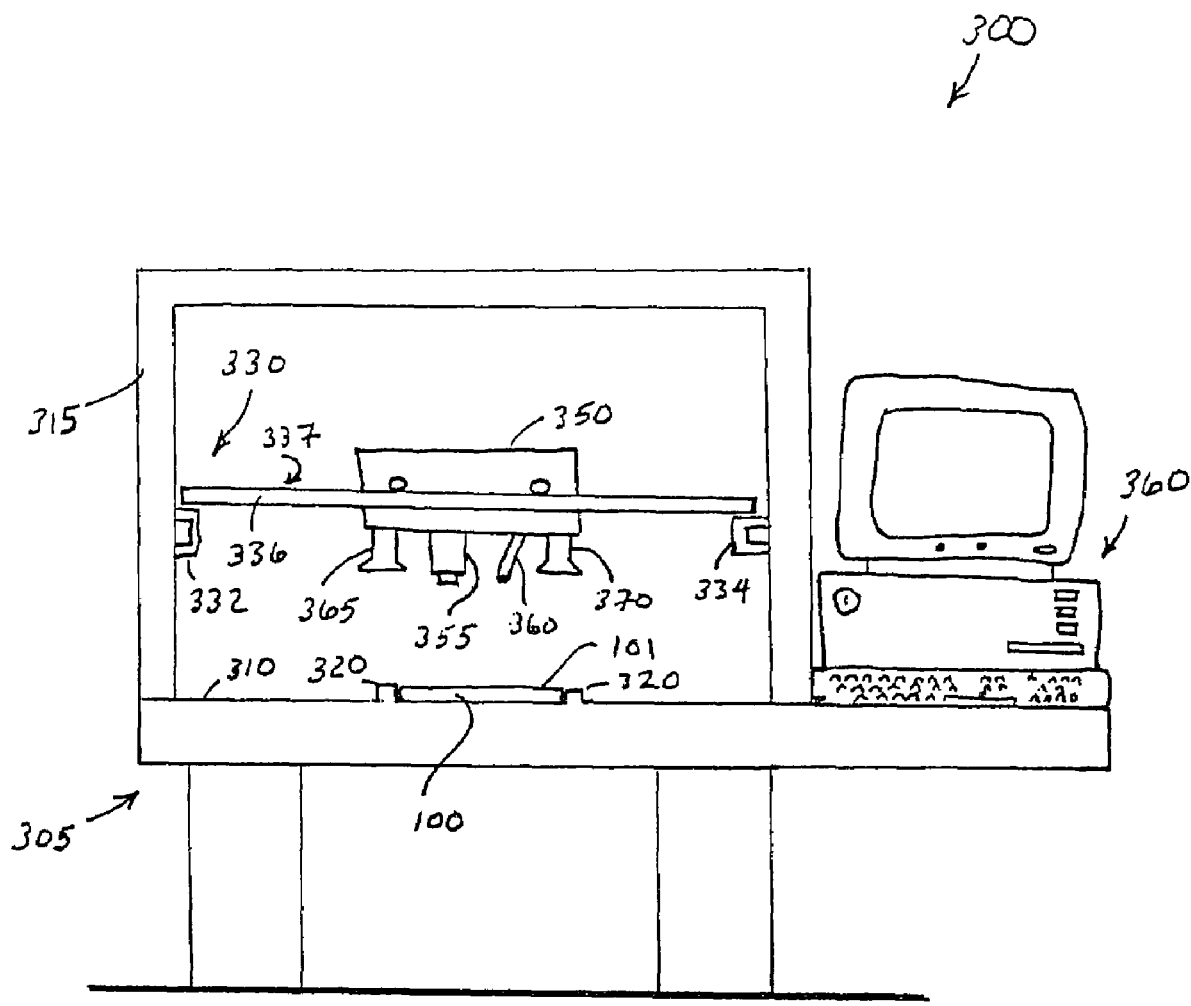
FIG. 3 is an illustration of an optical inspection platform configured in accordance with an embodiment of the present invention.

Semiconductor wafers that are being inspected are normally staged, that is, placed on a platform where they are held stationary or moved in a way that facilitates the inspections. FIG. 3 is an illustration of an optical inspection platform 300 configured in accordance with an embodiment of the present invention. Platform 300 includes a base 305 for support, and stage 310 on which the object to be inspected, in this case wafer 100, will be placed. Other objects may, of course, be inspected in like fashion. Enclosure 315 may be present to physically shelter the object being inspected and the optical platform 350, or to allow control of the inspection environment. Wafer 100 may be placed onto the platform by a human operator or by mechanical means, such as a robotic arm (not shown). Guides 320 or other suitable structures are formed in stage 310 to retain wafer 100 in the proper location for inspection.

Optical platform 350 is mounted above stage 310 on travel assembly 330 in such a way as to allow movement in one or more directions. Travel assembly 330 includes support rails 332 and 334, which are movably attached to enclosure 315 and operable to move upward and downward, raising and lowering optical platform 350. Travel arms 336 and 337(not visible in this view), are likewise mounted on rails 332 and 334 such that travel in a front-to-back direction is facilitated. Finally, optical platform 350 is mounted on travel arms 336 and 337 in such a way as to facilitate side-to-side movement. Travel assembly 330 thereby permits optical platform to be moved in any direction required to complete its scan of wafer 100. Preferably, a series of coordinated electric motors (not shown) are used to operate the various components of travel assembly 330. A computing device 360 may be used to coordinate motor operation to yield the desired direction of travel.

Optical platform 350 includes a camera 355 for capturing images of the surface being inspected. Camera 355 generally includes a number of charge-coupled devices (CCDs) as well as means for separating incoming light into different frequencies and directing each frequency to one or more of the CCDs (not shown). This, in effect, permits a number of different images to be captured at the same time. The incoming light in this case, of course, has been reflected from the surface of the object being inspected. Optical platform 350 also includes a plurality of light sources for illuminating the surface. In the configuration of FIG. 3, this includes a coherent light source 360 and two diffuse light sources 365 and 370, each of which emit light at a different frequency. Computing device 360 is also used to control the operation of the light sources 360, 365, and 370, and of the camera 355.

Figure 4:
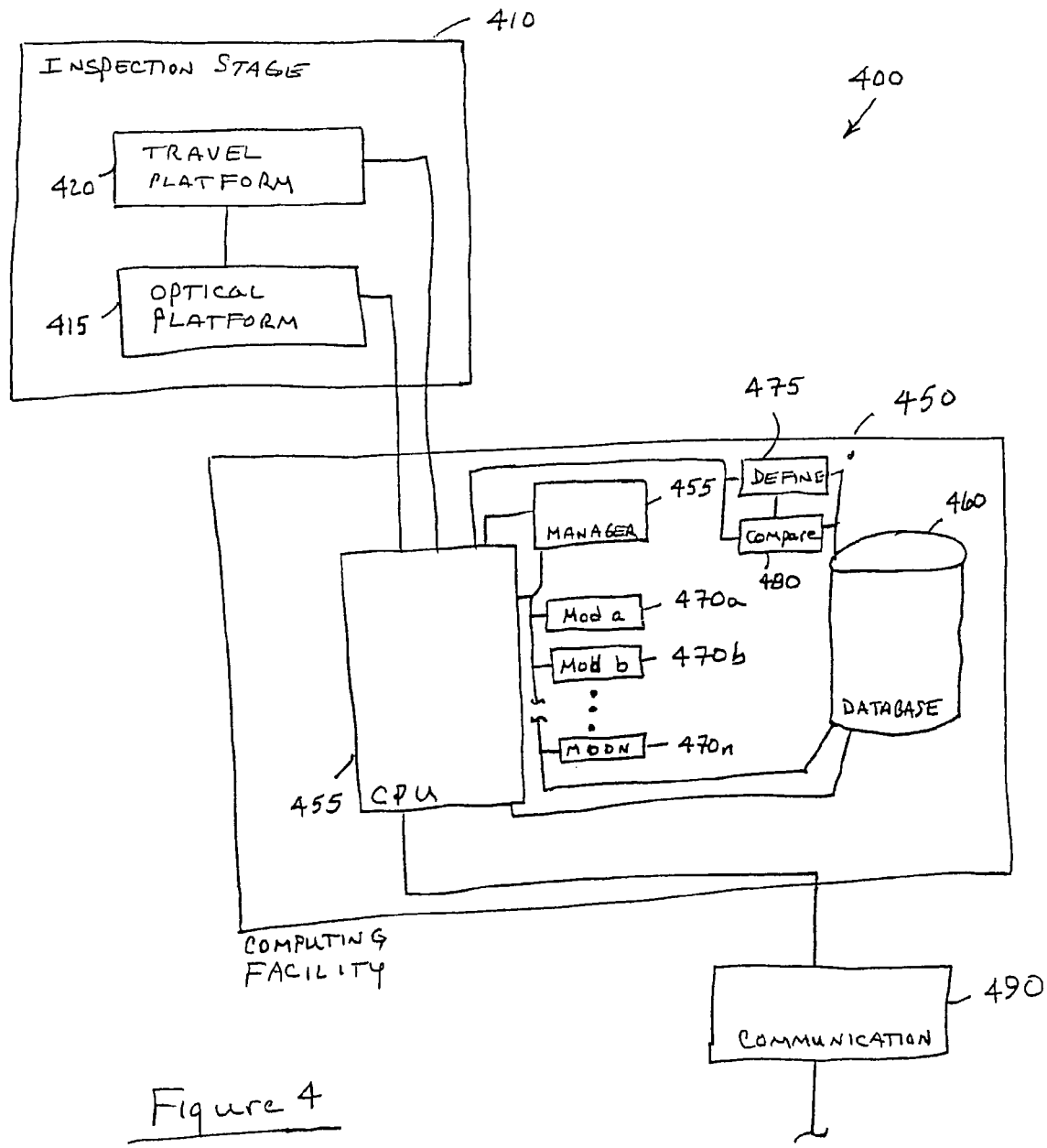
FIG. 4 is a simplified block diagram illustrating the relationship of selected components of an optical inspection system according an embodiment of the present invention.

FIG. 4 is a simplified block diagram illustrating the relationship of selected components of an optical inspection system 400 according an embodiment of the present invention. Although portions of some of these features have been described above, there will not necessarily be a one-to-one correspondence between components illustrated in FIG. 3 and the functional blocks of FIG. 4. In the embodiment of FIG. 4, inspection system 400 includes an inspection stage 410 and a computing facility 450. The inspection stage 410 includes an optical platform 415, which includes any number of illumination sources for illuminating the wafer during inspection and one or more image-capturing devices for capturing images of the illuminated wafer. Inspection system 400 also includes a travel platform 420, which is the electromechanical system that produces the relative motion, if any, between the wafer and the optical platform as is desired during the inspection. As alluded to above, this will normally involve movement of the optical equipment relative to a stationary wafer, but this is not necessarily the case. Travel platform 420 may also be used to properly position the wafer and the optical equipment even if there is no relative movement present when image capturing occurs.

In a preferred embodiment, the optical platform 415 includes light sources sufficient to emit diffuse light in at least two different wavelengths and coherent light in a third. These various light sources are then strobed as the optical platform 415 is moved in a scanning motion so that the camera captures numerous images of the wafer surface. Together, these images will form a composite image that can be evaluated for defects. The use of strobing and multiple wavelengths allows the system to capture multiple images of the same area during a single scanning movement.

The computing facility 450 of inspection system 400 includes a number of standard components including a central processing unit (CPU) 455 and a database 460. While each of these components has been represented as a single entity in FIG. 4, in another embodiment they may also comprise a number of different physical entities. By the same token, CPU 455 and database 460 may in some cases also be used to perform activities other than those associated with the inspection system.

Computing facility 450 also includes a number of specific modules that bear upon the operation of the inspection system 400 according to the present invention. As with the database and CPU, their function may be performed by one or more dedicated components, or by components that also perform other functions as well. The defect detection scheme manager 455 determines which defect detection scheme or schemes should be used examining a particular wafer. A set of detection schemes to be used on a particular wafer may be referred to as a defect detection scheme protocol. In accordance with the present invention, multiple defect detection schemes are programmed to be used on the same data set, running in parallel or serially to identify defects. By the same token, a particular defect detection scheme may be used to analyze data sets associated with all or only a portion of the semiconductor wafer or other object being inspected.

Computing facility 450 also includes a suite 470 of individual detection scheme modules, here represented by modules 470a, 470b, and 470n (indicating that any number ay be present. In a preferring embodiment, defect detection module suite 470 includes module for two-dimension histogram reference inspection, two-dimension histogram neighbor frame inspection, neighbor frame zero crossing inspection, neighbor frame medium inspection, neighbor frame plane inspection, neighbor frame statistic inspection, neighbor die zero crossing inspection, neighbor die medium inspection, neighbor die plane inspection, and neighbor die statistic inspection. These defect detection scheme modules are simply preferred; they are not required and others may be present as well.

In accordance with this embodiment of the present invention, a mask definition module 475 for defining the mask associated with each pixel or other defined image area. When the defect detection scheme protocol has been completed (or completed up to a pre-determined point), mask comparison module 480 is used to compare the currently-defined mask to a predetermined threshold. This comparison is made to determine whether the pixel is determined, within a range of confidence defined by the threshold, to be defective. Communication platform 490 includes transmitting and receiving equipment for communicating with a network and any peripheral devices associated with the system 400.

Figure 5:
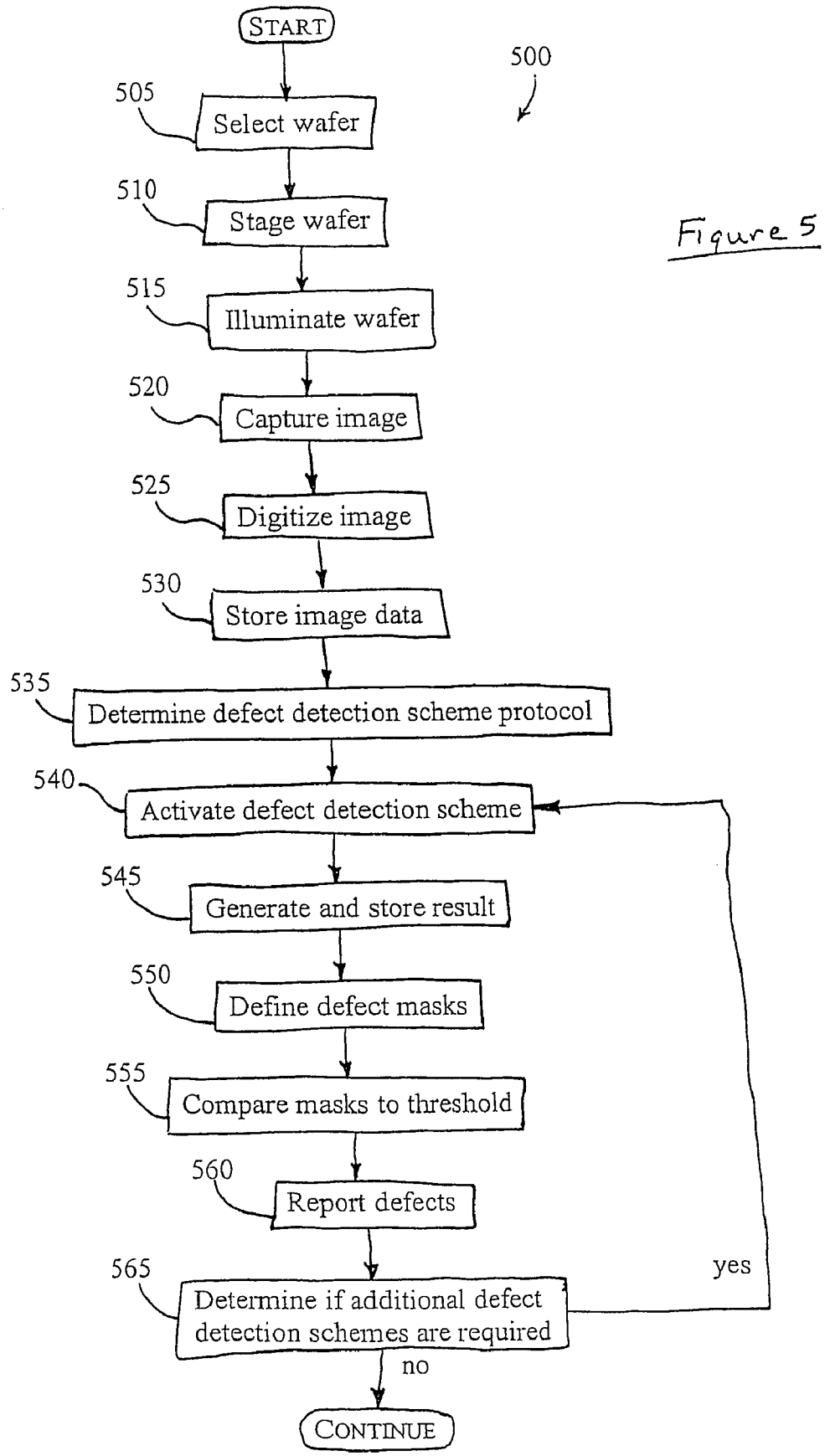
FIG. 5 is a flow diagram illustrating a method of inspecting the surface of an object according to an embodiment of the present invention.

FIG. 5 is a flow diagram illustrating a method of inspecting the surface of an object according to an embodiment of the present invention. As before, the method will be described in terms of semiconductor inspection although it is applicable in other environments as well. At START, it is presumed that an appropriate stage and optical platform has been provided, and configured to operate according to the present invention. In addition, the inspection hardware is in communication with a computing device that has been appropriately programmed and, in this embodiment, containing the modules described in reference to FIG. 4, above. The method begins with the selection of a wafer for inspection (step 505).

Wafer selection may be based any one or more of several criteria. Not-uncommonly, it is an arbitrary selection based only on meeting a requirement for selecting a certain number of samples from with in a given production run. In other applications, all wafers (or other objects) are inspected. In still other cases the specific object to be inspected may be chosen based on some previously-defined or calculated inspection criteria. For example if a wafer has previously failed an inspection and remedial action has been taken, the wafer may be automatically selected for inspection at subsequent opportunities.

However the selection is made, the process continues with physically staging the object (step 510). Staging may be accomplished in-line or off line. For in-line inspection, appropriate images are captured while the object is still in the normal production line or location. Note that in reciting the claims of the present invention, this will still be considered 'staging' even though the system in reality simply waits to begin until the object has reached an appropriate position. When staging is off-line, a separate staging platform is typically provided so that the selected object may be manually or by robotic arm or similar device may be moved into position for inspection. (See, for example, FIG. 3.)

When the wafer or other object has been staged, it is scanned by the optical equipment (steps 515 and 520). A scan preferably includes one, but may include multiple passes with the inspection equipment. Note that in a preferred embodiment, the optical equipment (examples of which having been described above) moves with respect to the wafer but the wafer may also move. Naturally, it is the relative movement that is of consequence. In some applications, no relative movement at all is required, but this is the exception rather than the rule. The relative motion of the object and the optical equipment during scanning, if performed, may be accomplished by lateral or angular movement. That it, the optical equipment may be mounted on a travel assembly (as in FIG. 3), or it may be fixed so that it des not change location but simply swivels, sweeps, or rotates, as necessary to perform the required scan.

The optical equipment preferably includes a camera and one or more sources of illumination, as explained in connection with FIG. 3 above. In a preferred embodiment, the camera and illumination sources are mounted together on a platform that moves relative to the staged wafer. The illumination sources include a coherent light source and a more diffuse light source, the former for creating a point, line or grid pattern, as desired, on the surface of the object being inspected and the latter for illuminating the entire surface or a large portion thereof. For the camera to capture an image created by each individual light source, each of the multiple illumination sources use different wavelengths of light or are strobed on and off at different times, or both. When different wavelengths are used, the camera is operable to separate the different images by wavelength.

Whatever the configuration of the optical platform, the process continues with the illumination of all or part of the surface being inspected (step 515). Note that this step may actually included several illumination steps (not shown individually) in accordance with the specific design parameters involved. While the surface is being illuminated, images formed by reflected light are captured (step 520). The image-capturing step 520 will include the collection of an appropriate number of images depending on the types of illumination used. The captured image or images are then digitized (step 525) and stored on an electronic storage device (step 530).

Next, the inspection system determines the defect detection scheme protocol for the wafer being inspected (step 535). The protocol, as alluded to previously, may be the same for each wafer being inspected, though there may be reasons to individualize the protocol as well. The defect detection scheme protocol for a particular case may indicate that only one defect detection scheme is used, but the advantages of the present invention are more fully realized when a number of schemes are employed. The different defect detection schemes may be applied to the data at the same time or one after the other in a pre-determined or random order. They each may use all or only a portion of the data captured for the wafer. Naturally, they may also refer to data related to the wafer that was previously captured and stored, if such data exists. The defect detection scheme protocol may include an indication of whether this 'history' or only current data is to be used.

Note in this regard that running two or more defect detection schemes at the same time means only that they are permitted to be run at the same time; the capacity of the computing facility may well determine how many modules may actually be activated simultaneously. the defect detection scheme protocol may include an indication of whether the defect detection schemes are applied serially or in parallel.

One or more defect detection scheme modules are then activated (step 540), depending on the indications of the selected protocol. The module or modules use the data associated with the wafer as is also prescribed in the protocol. The different data potions available to the data detection module being run are those images associated with the different light frequencies or strobe intervals as described above. For convenience, each unique set of data will be referred to as having been obtained via a separate channel, whether this channel was created by using a particular wavelength or a certain time of capture. Data associated with the same channel may not all be collected simultaneously, however, as when a laser line is scanned across the wafer surface and a composite image is then assembled. When at least one defect detection scheme has been run using the prescribed data, it generates a result that is then stored for future use (step 545). The result will include a listing of those defects that have been found for each pixel (or some other identifiable data unit). If dictated by the protocol, the same defect detection module may be applied to other sets of data as well, and the results stored (steps not shown).

A defect mask is then defined for each pixel in the captured image (step 550). (Note that in an alternate embodiment (not shown) defect masks are created for other image subdivisions instead of at the pixel level.) Each algorithm and channel is given a weight that scales the identified defect pixels and provides the appropriate detection power. These weights are typically assigned in advanced but could also be altered during the inspection process. For example, if image data associated with a particular channel is determined to be less than optimum, the weight of any results applying that date could be reduced. This may be done automatically or upon receiving an appropriate response to an operator query. Weights, of course, may be positive or negative, with a defect ultimately indicated by a defect mask value respectively above or below a threshold. In some cases a combination of results may be assigned a weight. As a simple illustration, modules 470a and 470b (shown in FIG. 4) may each be assigned a weight of 3, but if both indicate a defect is present, a total weight of 7 may be added to the mask. Or conflicting results between two or more specific modules may result in a defect mask adjustment greater then the sum of their individual weights. Other combinations are possible, of course.

In one embodiment (not specifically illustrated), the defect masks are created as follows. A two-byte (HI,LO) defect mask is defined for each pixel within the image. For each pixel, the algorithm weights are added together and stored in the LO byte, and the corresponding added channel weights are stored in the HI byte. Variable thresholds are defined for the HI and LO bytes thereby determining the confidence level for the defect identified. Sensitivity and robustness can be varied as follows: a defect candidate is considered valid if it occurs in any channel/algorithm (most sensitive) to a defect candidate is considered valid only if it occurs in every channel and all algorithms (most robust). Confidence in detected defects is built, for example, by comparing multiple color channels and using multiple detection modes for each channel. Note, however, that while the method of the present invention is frequently applied using a multicolor system, other types of systems can be used as well. By the same token, defect masks are not limited to the embodiment described above.

However developed, the defect mask associated with each pixel or other defined area suspected to include a defect is then compared to a predetermined threshold (step 555). Naturally, if no combination of defect detection scheme and channel has indicated the presence of a defect, then the area may be presumed with a high degree of confidence to be defect-free. For other areas, if the defect mask is within the threshold, the area is also considered to be defect free. If, on the other hand, the defect is beyond the threshold, a defect is reported (step 560).

At this point it is determined whether additional defect detection scheme modules are to be applied to one or more sets of data (step 565). If so, the process returns to step 540 and activates the appropriate module or modules. Steps 545 through 565 are then repeated. If it is determined at step 565 that no further defect detection scheme modules need to be activated, then the process continues with the next step (not shown) as dictated by the defects reported in step 560. This may include discarding the wafer, marking certain dice for discard, repair, or simply returning the wafer to (or continuing) the production process.

Note that the steps of method 500 are organized in a certain sequences, but other sequences are possible and in accordance with the present invention. For example, the mask comparison step 555 and the defect reporting step 560 could be performed only after all required modules have been applied to all of the indicated data. The advantage performing these steps multiple times is that the process may be terminated early if the indicated threshold is reached before each module is activated. This might be expected in the case of a severe or very obvious defect.

In an alternate embodiment (not shown), the value of the threshold may be dynamically adjusted if certain results are obtained. Naturally, the system operator may adjust the protocols and thresholds at any time, but at some times it may be advantageous to do so automatically, based on the result of a certain inspection or the cumulative result of a number of inspections. For example, if the application of certain modules (or a certain number of modules) to selected data sets produce conflicting results, the threshold may be adjusted automatically or in response to a query set to the system operator. In another embodiment (also not shown), the protocol itself is altered or replaced with a different protocol based on events such as are described above. In any embodiment, instead of simply identifying defects associated with masks that or beyond a threshold value, the system may also report all (or selected) defects and their associated mask values so that the system operator may finally determine which defects should be confirmed.

Figure 6:
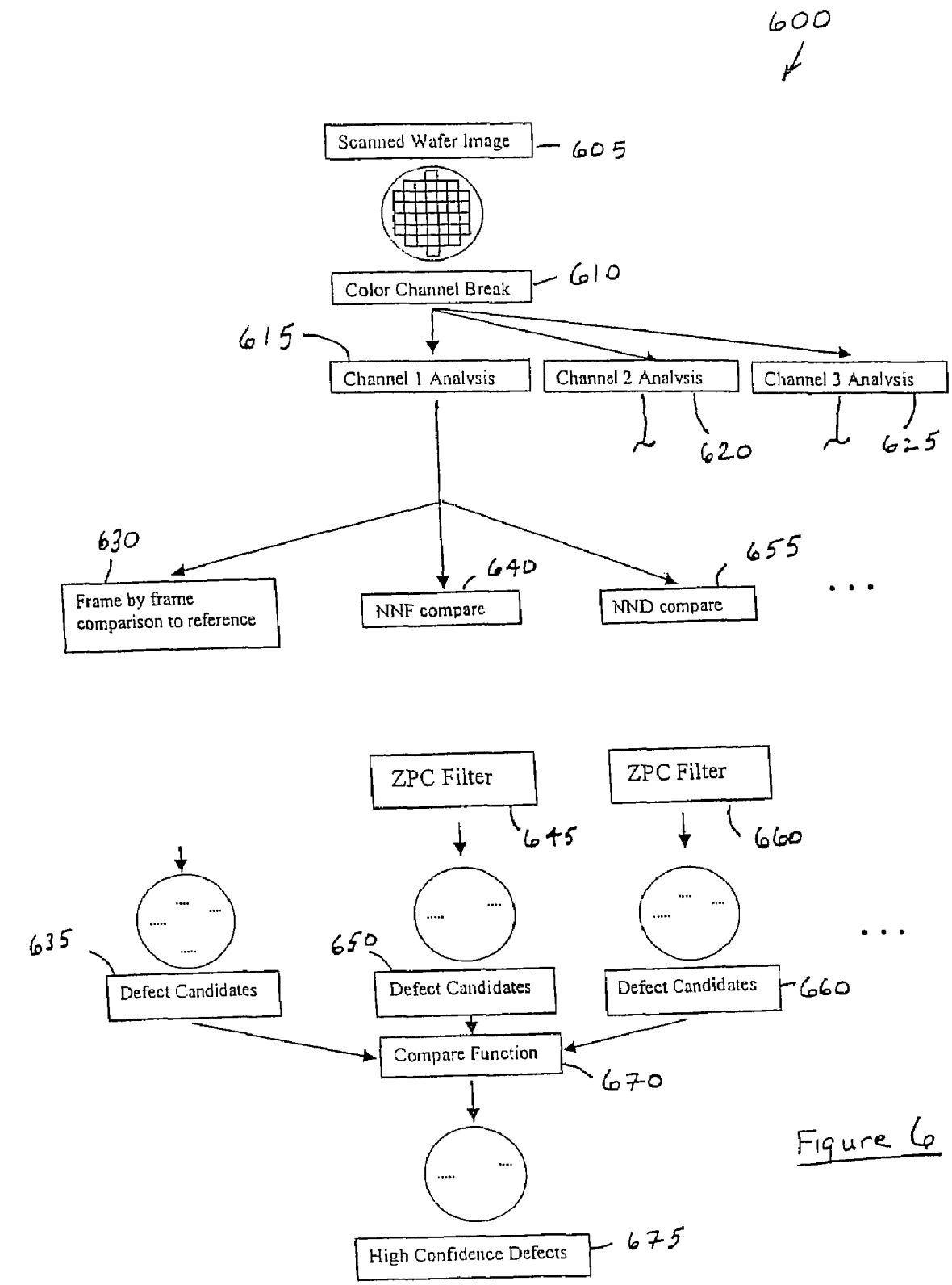
FIG. 6 is a simplified process flow diagram illustrating a method according to one embodiment of the present invention.

FIG. 6 is a simplified process flow diagram graphically illustrating a method 600 according to one embodiment of the present invention. Block 605 represents a scanned wafer image, which may include a plurality of wavelengths of light. The image is them broken down by wavelength (block 610) into its component images for separate analysis (blocks 615, 620, and 625). In this embodiment, channel 1 (data associated with one of the component images) is subject to a frame-by-frame comparison to an ideal reference (block 630) and defect candidates are identified (block 635).

In addition, the channel 1 data is analyzed using a nearest neighbor frame (NNF) comparison (block 640). A zero point crossing filter is applied to the result (block 645), and candidate defects are identified (block 650). In the embodiment of FIG. 6, the channel 1 data is also analyzed using a nearest neighbor die (NND) comparison (block 655). A zero point crossing filter is applied to the result (block 660), and candidate defects are identified (block 665). Other defect detection scheme modules may also be applied. The data from channels 2 and 3 may also be analyzed in the same fashion, or by using a different set of defect detection schemes. The defect candidates from each (or selected ones) of these analyses are then compared (block 670) and defects that can be identified with a high degree of confidence are reported (block 675).

In general, the system of the present invention incorporates a comparison function, which may be applied using any of several approaches. Defective pixel candidates from each channel or algorithm are compared with one another to determine if the candidate defect passes a predetermined robustness test. In particular, if a defect only occurs for a certain channel, or certain algorithm, then it may not be a defect. Conversely, if the defect occurs in many channels and is detected by numerous algorithms, then the likelihood of the candidate defect being a real defect has increased. Application of the present invention thereby increases manufacturing efficiency by provide a higher degree of confidence in the accuracy of the defect detection system, and by reducing the need for any individual defect detection scheme to employ elaborate filtering mechanisms in an attempt to reduce erroneous results.

Note that these examples are for purpose of illustration, however, and not limitation; other variations are possible. Rather, descriptions above are of examples for implementing the invention, and the scope of the invention should not necessarily be limited by this description. Rather, the scope of the present invention is defined by the following claims.

What is claimed is:

1. A method of inspecting an object, comprising the steps of:

providing an optical inspection system comprising a staging platform, an optical platform, and a computing facility, the computing facility comprising a database for storing programs and collected data;

staging the object;

scanning the object by illuminating at least a portion of the surface of the object and capturing at least one image created by light reflected from the surface of the object;

storing data representing the at least one image captured in the scanning step;

selecting a defect detection protocol comprising a plurality of defect detection algorithms;

analyzing the collected data using the selected plurality of defect detection algorithms;

assigning a first weight to a first defect detection algorithm and a second weight to a second defect detection algorithm, the first weight and second weight being different and the first defect detection algorithm and second defect detection algorithm being part of the plurality of defect detection algorithms;

building at least one defect mask, wherein each defect mask corresponds to a specific portion of the object surface being inspected and has a value determined by weights assigned to the plurality defect detection algorithms; and determining the existence of a defect based on the defect mask.

2. The method of claim 1, wherein the object is a semiconductor wafer.

3. The method of claim 1, wherein the plurality of defect detection algorithms are used substantially in parallel.

4. The method of claim 1, wherein at least one of the plurality of defect detection algorithms is not used until after another of the plurality of defect detection algorithms has been used.

5. The method of claim 4, wherein the plurality of defect detection algorithms are run serially.

6. The method of claim 4, wherein the step of determining the existence of a defect comprises comparing the at least one defect mask to a predetermined threshold and is performed prior to using all of the plurality of defect detection algorithms.

7. The method of claim 6, further comprising the step of terminating inspection process in the event that the at least one defect mask is beyond the predetermined threshold.

8. The method of claim 1, wherein the step of scanning the object comprises illuminating a surface of the object with light from a plurality of sources, each source emanating light at wavelength different than that of the other sources.

9. The method of claim 8, wherein the step of scanning further comprises separating the reflected light so that multiple images may be captured.

10. The method of claim 8, wherein the scanning step further comprises strobing the light from at least one of the plurality of light sources.

11. The method of claim 1, further comprising:
reporting existence of a defect based upon the determination.

12. The method of claim 1, wherein the assigned weights are indicative of a likelihood that a possible defect implicated by the corresponding defect detection algorithm is an actual defect.

13. The method of claim 1, wherein building at least one defect mask includes:
obtaining analyses from at least two default detection algorithms at least one of which implicates a possible defect;
assigning at least one weight value to at least one of the analyses; and
combining the analyses and the at least one weight value to generate the defect mask.

14. A system for inspecting the surface of an object, comprising:
an optical platform for scanning the surface; and
a computing facility for analyzing data collected when the surface is scanned, wherein the computing facility comprises a plurality of defect detection scheme modules for analyzing the collected data and a defect detection scheme manager for selecting which of the plurality of defect detection scheme modules to apply to the collected data; and
wherein the analysis comprises applying the selected defect detection scheme modules and building at least one defect mask, wherein each defect mask corresponds to a specific portion of the object surface being inspected and has a value determined by weights assigned to each of the defect detection modules applied to the collected data, wherein a first weight assigned to a first defect detection module is different from a second weight assigned to a second defect detection module.

15. The system of claim 14, wherein the optical platform comprises a plurality of light sources, each source emanating light at wavelength different than that of the other sources.

16. The system of claim 15, wherein at least one of the light sources is strobed at a predetermined rate.

17. The system of claim 15, wherein the optical platform further comprises a camera having a plurality of charge-coupled devices (CCDs) for capturing images and means for separating incoming light into component wavelengths and directing each component to one of the plurality of CCDs.

18. The system of claim 15, wherein the collected data is separated into subsets, each subset corresponding to an image created by light of a certain wavelength.

19. The system of claim 18, wherein defect detection scheme manager determines which of the plurality of defect detection modules, if any, will be applied to each data subset.

* * * * *

UNITED STATES PATENT AND TRADEMARK OFFICE
CERTIFICATE OF CORRECTION

| | | |
|---|---|---|
| PATENT NO. | : 7,539,583 B2 | Page 1 of 1 |
| APPLICATION NO. | : 11/201279 | |
| DATED | : May 26, 2009 | |
| INVENTOR(S) | : Yonghang Fu, Yongqiang Liu and Michael J. Darwin | |

It is certified that error appears in the above-identified patent and that said Letters Patent is hereby corrected as shown below:

Column 2, line 11, delete "these" and insert in place thereof --These--.

Column 8, line 35, delete "the" and insert in place thereof --The--.

Column 9, line 15, delete "(HI,LO)" and insert in place thereof --(HI, LO)--.

Column 10, line 19, delete "them" and insert in place thereof --then--.

Signed and Sealed this

Twenty-first Day of July, 2009

JOHN DOLL
*Acting Director of the United States Patent and Trademark Office*